United States Patent [19]

Larkins et al.

[11] Patent Number: 4,886,878

[45] Date of Patent: Dec. 12, 1989

[54] MODIFIED ZEIN GENES CONTAINING LYSINE

[75] Inventors: Brian Larkins, Tucson, Ariz.; Richard E. Cuellar, Glen Ellyn, Ill.; John C. Wallace, West Lafayette, Ind.; Gad Galili, Rehovot, Israel

[73] Assignees: Lubrizol Genetics, Inc., Wickliffe, Ohio; Purdue Research Foundation, Inc., West Lafayette, Ind.

[21] Appl. No.: 274,828

[22] Filed: Nov. 22, 1988

Related U.S. Application Data

[63] Continuation of Ser. No. 929,751, Nov. 12, 1986, abandoned, which is a continuation-in-part of Ser. No. 744,913, Jun. 12, 1985, abandoned.

[51] Int. Cl.[4] .................... C07H 23/00; C07H 19/06; C07H 15/12

[52] U.S. Cl. .................................. 536/26; 536/27; 536/28; 536/29; 435/172.3

[58] Field of Search .................... 536/26, 27, 28, 29; 530/372, 373; 435/172.3

[56] References Cited

U.S. PATENT DOCUMENTS 4,431,739 2/1984 Riggs .................................. 435/253

FOREIGN PATENT DOCUMENTS

83/01176 4/1983 PCT Int'l Appl. .

OTHER PUBLICATIONS

Weinard et al "Cloning of double stranded DNAs derived from polysonal in RNA of maize endosperm:isolation and characterization of zein clones" Nuc. Acid Res. vol. 6, No. 8, pp. 2707–2715, 1979.

Messing et al (1983) Genetic Engineering of Plants An Agricultural Perspective Plenum Press, p. 211–227.

Kalmnikov et al C.A. 95:P397, abstract no. 200780c.

Messing (1983) Trends in Biotechnology 1(2): 54–59.

Larkins et al (Mar., 1985) Federation Proceeding: 69th Annual Meeting, Anaheim, CA 44 (3):649 abstract no. 1396.

Coraggio et al (1986) Genetica Agraria 40(4):443–444.

Corragio et al. (1985) Genetica Agraria 39(3): 318.

Viotti et al. (May, 1985) EMBO J. 4(5): 1103–1110.

Norrander, (1984) Dissertation Abstracts International 45 (12, part 1):3805.

Kalininkov et al (1980) Method Radiobiol. v. Selektski: Genet. S.-kh Rast. Kishinev 32–35. (in Russian with English translation).

Polacco (1984) Applications of Genetic Engineering to Crop Improvement (Collins et al, Eds) Martinus Nijhoff/Dr. W. Junk Pub., Dordnecht, The Netherlands pp. 255–304.

*Primary Examiner*—John Kight
*Assistant Examiner*—Nathan M. Nutter
*Attorney, Agent, or Firm*—Greenlee and Associates

[57] ABSTRACT

Modified 19kd and 22kd zeins containing lysine are provided. Lysine additions are made by modifying structural genes which encode 19kd and 22kd pre-zeins. Modified zeins produced from the modified structural gene templates are found to retain important properties of unmodified zeins, having similar molecular weights, having the ability to form protein bodies within the rough endoplasmic reticulum of a host cell and being soluble in alcohol.

10 Claims, 10 Drawing Sheets

FIG. 1

Consensus Amino Acid Sequence of Zein Proteins

| Zein protein | | Sequence positions |
|---|---|---|
| | Signal Sequence | |
| Z22 | M A T K I L S L L A L L A L F A S A T N A | 1-21 |
| Z19 | M A A K I F C L I M L L G L S A S A A T A | 1-21 |
| | N-Terminal Turn | |
| Z22 | S I I P Q C S L A P . S S I I P Q F L P P V T S M A F E H P A V Q A Y R | 22-56 |
| Z19 | S I F P Q C S Q A P I A S L L P P Y . S P A M S S V C E N P I L L P Y R | 22-57 |
| | Repeat Sequences | |
| Z22 and Z19 9 repeats | Q Q F/L L P A/F N Q L A/L A/V A N S P A Y L Q Q | 57-237 58-225 |
| | C-Terminal Turn | |
| Z22 | Q Q Q L L P Y N R F S L M N P V L S R Q Q P I V G G A I F | 238-266 |
| Z19 | . . . . . . . . . . . . . . . . . . . Q Q P I I G G A L F | 226-235 |

FIG. 2-1

```
                                                                           Met
       -65                                                              -1+1
cZ19A2                                       .                   .             START :                 T   C
cZ19B1  START:                              C                   G        C                                  C
gZ19AB1       ATCGCACATATTATTGAGACCAACTAGCAATATAGAAAGCA****CAATATTGTACCAATA ATG GCA GCC AAA ATA TTT TGC CTC ATT ATG CTC CTT GGT
cZ19D1                                  ACATAGTGAAGTACACTAGCAACATCTTAGCACCA ATG GCA GCC AAG ATT TTT GCC CTC CTT GCC CTC CTT GCT    + 39
cZ19C2                       ACAAGCAACATAGAAAGTGGAATCCAGTAGCAACAATAGAGCAACA ATG GCG ACC AAG ATA TTT TCC CTC CTT ATG CTC CTT GCT
cZ19C1                      START:                               C
                                          NH2-

cZ19A2                             C       C                                          A                                         A
cZ19B1                                     C                       G                                        G              T
gZ19AB1   CTT TCT GCA AGT GCT GCT ACG GCG AGC ATT TTC CCG CAA TGC TCA CAA GCT CCT ATA GCT TCC CTT CTT CCC CCA TAC CTC TCA CCA GCG
cZ19D1    CTT TCA GCA AAC GTT GCT ACC GCG ACT ATT ATT CCA CAA TGC TCA CAA *** *** *** *** *** *** *** *** CAA TAC CTC TCT CCG GTG   +129
cZ19C2    CTT TCT ACA TGT GTT GCT AAC GCG ACA ATT TTC CCT CAA TGC TCA CAA GCT CCT ATA GCT TCC CTT CTT CCC CCA TAC CTT CCA TCA ATT
cZ19C1            G                                                                                                             G

cZ19A2    G             G          C               A
cZ19B1    G         G              C        C      A                                        T
gZ19AB1   ATG TCT TCA GTA TGT GAA AAT CCA ATT CTT CTA CCC TAC AGG ATC CAA CAG GCA ATC GCA GCA GGC ATC TTA CCT TTA TCA CCC TTG TTC
cZ19D1    ACA GCC GCG AGA TTT GAA TAC CCA ACT ATA CAA TCC TAC AGG CTA CAA CAG GCC ATC GCA GCA AGC ATC TTA CGG TCG TTA GCA TTG ACT   +219
cZ19C2    ATA GCT TCA ATA TGT GAA AAC CCA GCT CTT CAA CCA TAT AGG CTT CAA CAA GCA ATC GCA GCA AGC AAC ATA CCT TTA TCG CCC TTG TTG
cZ19C1                G                             G   C

cZ19A2                C G                                                                       T                               T
cZ19B1                                                                  A                                                       T
gZ19AB1   CTC CAA CAA TCA TCA GCC CTA TTA CAA CAG TTA CCT TTG GTG CAT TTG TTG GCA CAA AAC ATC AGG GCA CAA CAA CTA CAA CAA CTC GTG
cZ19D1    GTC CAA CAA CCA TAT GCC CTA TTG CAA CAA CCA TCC TTA GTG AAT CTA TAT CTC CAA AGA ATC GTA GCA CAA CAA CTA CAA CAA CAA TTG   +309
cZ19C2    TTT CAA CAA TCG CCA GCC CTA *** *** *** *** TCT TTG GTG CAG TCA TTG GTA CAA ACC ATC AGG GCA CAA CAG CTG CAG CAA CTC GTG
cZ19C1
```

FIG. 2-2

```
cZ19A2                                                G                A                  T           T                    G
cZ19B1                                                                                    T           T                       G  T
gZ19AB1  CTA *** *** *** *** *** *** *** *** GCA AAC CTT GCT GCC TAC TCT CAG CAA CAA CAG TTT CTG CCA TTC AAC CAA CTA GCT GCA TTG
cZ19D1   CTT CCA ACA ATC AAT CAA GTA GTT GCA GCG AAC CTT GAT GCT TAC CTC CAG CAA CAA CAA TTT CTT CCA TTC AAT CAA CTA GCT GGG GTG
cZ19C2   CTA CCT CTG ATC AAC CAA GTA GCT CTG GCA AAC CTT TCT CCC TAC TCT CAG CAA CAA CAA TTT CTT CCA TTC AAC CAA CTG TCT ACA CTG  +399
cZ19C1

cZ19A2                           *** ***      A                                                            A
cZ19B1                T           A  ***      A                                       C                    A
gZ19AB1  AAC TCT GCT GCT TAT TTG CAG CAA CAA CAA CTA CTA CCA TTC AGC CAG CTA *** *** *** GCT GCT GCC TAC CCC CGG *** *** CAA TTT
cZ19D1   AAC CCT GCT GCT TAC TTG CAG GCA CAA CAG CTA CTA CCA TTC AAC CAA CTT GTC AGG AGC CCT GCT GCC TTC TTA CTG CAG CAA CAG TTG
cZ19C2   AAC CCT GCT GCT TAT TTG CAG *** CAA CAA CTA TTA CCA TTT AGC CAG CTA *** *** *** GCT ACT GCC TAC TCT CAG CAA CAA CAA CTT  +489
cZ19C1

cZ19A2                T                              GC          T         G      G       C                           A
cZ19B1                                                C          T         G                                          G
gZ19AB1  CTT CCA TTC AAC CAA CTG GCA GCA TTG AAC TCT CAT GCT TAT GTA CAA CAA CAA CAA CTA CTA CCA TTC AGC CAG CTA GCT GCT GTG AGC
cZ19D1   TTG CCA TTC CAT CTA CAA GTT GTG GCA AAC ATT GCT GCT TTC TTG CAA CAA CAA CAA TTG CTG CCA TTT TAC CCA CAG GTT GTG GGA AAC
cZ19C2   CTT CCA TTT AAC CAA TTG GCC GCA CTG AAC CCC GCT GCT TAT TTG CAG CAG CAA ATA CTA CTA CCA TTT AGC CAG CTA GCT GCA GCA AAC  +579
cZ19C1

cZ19A2                                                 A                 G                C          G
cZ19B1           A                A   C                           A      GT               C
gZ19AB1  CCT GCT GCC TTC TTG ACA CAG CAA CAG TTG TTG CCG TTC TAC CTG CAC ACT GCG CCT AAC GTT GGC ACC CTC TTA CAA CTG CAA CAA TTG
cZ19D1   ATT AAC GCC TTC TTG CAA CAG CAA CAG TTG CTG CCA TTC TAC CCA CAG GAT GTG GCA AAC AAT GTC GCC TTC TTA CAA CAA CAA CAA TTG
cZ19C2   CGT GCT TCC TTC TTG ACA CAG CAA CAG TTG CTG CCT TTC TAC CAG CAG TTT GCG GCT AAC CCC GCA ACC CTC TTA CAA CTA CAA CAA TTG  +669
cZ19C1
```

FIG. 2-3

```
                                                                                                            -COOH
cZ19A2                                              A
cZ19B1              A                                    T
gZ19AB1 CTG CCA TTC GAC CAA CTT GCT TTG ACA AAC CCA GCA GCG TTC TAC CAA CAA CCC ATC ATT GGT GGT GCC CTC TTT TAG
cZ19D1  CTG CCA TTT AGC CAA CTT GCT TTG ACG AAT CCT ACC ACC TTA TTG CAG CAG CCC ACC ATT GGT GGT GCC ATC TTC TAG   +747
cZ19C2  TTG CCC TTT GTC CAA CTT GCT TTG ACA GAC CCA GCG GCC TCC TAC CAA CAA CAC ATC ATT GGT GGT GCC CTC TTT TAG
cZ19C1

cZ19A2                             G         G A    G                                  An:end
cZ19B1     T                                 AT     G                                         An:end
gZ19AB1 ATTGCTTATGAGTTATAGTTCAATAATAAAGTTTTTTTGCTGATATTTGTGGCTTCCCAGAAATAAGAAAGTACATTTCTAGATTCTTATGTGCTTCTAGTCTCCAA.. +854
cZ19D1  ATTTTTTATGCTTTATACTGTAATAATAAAGTTCTCATACTGATATGTGCAACTTCTCAGTAATAAAAGATTAGAGATCTATATTTTATTA:end
cZ19C2  ATTGCTTATTAGTTGTAATTCAATAATAAAGTTTTTTGGATGATGTATGTGGCCAACCAGAAATAAGAAGTTACATTTCCAn:end
cZ19C1                                                                                     AGATTCTAATGTGATATTGGT
```

```
                                                                            Met
        -67                                                             -1+1
        .      .         .         .         .         .         .        . .
cZ22A1  TCTCCCATAATATTTTCAGCATTCAAAAACACACCAAGCGAAGCGCACTAGCAACGACCTAACACCA ATG GCT ACC AAG ATA TTA GCC CTC CTT GCG CTT CTT GCC
cZ22B1                                                 start:  A        A                           T                         G    + 39
cZ22C2                                                                                  start:
                                        NH2-
cZ22A1  CTT TTA GTG AGC GCA ACA AAT GCG TTC ATT ATT CCA CAG TGC TCA CTT GCT CCT AGT GCC AGT ATT CCA CAG TTC CTC CCA CCA GTT ACT
cZ22B1        T  C                      C               A                           T    T                                         +129
cZ22C2        T                                         A                                T    A

cZ22A1  TCA ATG GGT TTC GAA CAT CCA GCC GTG CAA GCC TAC AGG CTA CAA CTA GCG CTT GCG GCG AGC GCC TTA CAA CAA CCA ATT GCC CAA TTG
cZ22B1           CC           C       T               T              A      A                T                                     +219
cZ22C2            C           C  T    T                              A                A      T                      AA

cZ22A1  CAA CAA CAA TCC TTG GCA CAT CTA ACC CTA CAA ACC ATT GCA ACG CAA CAA CAA CAA CAA CAG TTT CTG CCA TCA CTG AGC CAC CTA GCC
cZ22B1                                    A A            C                    G ***              C   A      G                      +309
cZ22C2                                      A            C                    G ***              C   A      G         A      AT

cZ22A1  ATG GTG AAC CCT GTC ACC TAC TTG CAA CAG CAG CTG CTT GCA TCC AAC CCA CTT GCT CTG GCG AAC GTA GCT GCA TAC CAG CAA CAA CAA
cZ22B1                      G                                                         A   A          T      A                      +399
cZ22C2  G                   G                                                             A                       A
```

FIG. 3-1

```
cZ22A1  CAG CTG CAA CAG TTT ATG CCA GTG CTC AGT CAA CTA GCC ATG GTG AAC CCT GCC GTC TAC CTA *** *** *** CAA CTA CTT TCA TCT AGC
cZ22B1    A                 C        C    T                                      C          CAA CAG CAA       G                 +489
cZ22C2    A T     G         C        C                                           C          CAA CAG CAA       G

cZ22A1  CCG CTC GCG GTG GGC AAT GCA CCT ACG TAC CTA CAA CAA CAG TTG CTG CAA CAA ATT GTA CCA GCT CTG ACT CAG CTA GCT GTG GCA AAC
cZ22B1            T      C                A       G         G A     T         G                  A                              +579
cZ22C2    T       T       T               A       G           A               G

cZ22A1  CCT GCT GCC TAC TTA CAA CAG TTG CTT CCA TTC AAC CAA CTG GCT GTG TCA AAC TCT GCT GCG TAC CTA CAA CAG CGA CAA CAG TTA CTT
cZ22B1       T            G         C                         A A   A     G          T                                          +669
cZ22C2                    G         C                           A         G

cZ22A1  AAT CCA TTG GCA GTG GCT AAC CCA TTG GTC GCT ACC TTC CTG CAG CAG CAA CAA CAA TTG CTG CCA TAC AAC CAG TTC TCT TTG ATG AAC
cZ22B1                                              G         A         ***                              G                      +759
cZ22C2          C A  A      C A                     GG        A         ***                  A       G                        T
                                                           -COOH

cZ22A1  CCT GCC TTG *** *** CAG CAA CCC ATC GTT GGA GGT GCC ATC TTT TAG ATTACATATGAGATGTACTCGACAATGGTGCCCTCATA:end
cZ22B1       T      TCG AGG                                                                    T               CCGGCATGTGTTTCCTA   +862
cZ22C2              TCG TGG                                                                    T               CCGGCATGTGTTTCCTA

cZ22B1  GAAATAATCAATATATTGGTGAn
cZ22C2  GAAATAAACAATATATTGATTGAGATTTATCTCGATATATTGTTGAACTATGTTCATCATATAAATAATTGAAAACATCAAATCGTAATTATAAACTAn             +960
```

```
cZ19A2   START :   FL                T           T          V          Q                    P
cZ19B1              L                T                    S V          Q
cZ19AB1    MAAKIFCLIM LLGLSASAAT ASIFPQCSQA PIASLLPPYL SPAMSSVCEN PILLPYRIQQ AIAAGILPLS PLFLQQSSAL LQQLPLVHLL AQNIRAQQLQ
cZ19D1     MAAKIFALLA LLALSANVAT ATIIPQCSQ* *******QYL SPVTAARFEY PTIQSYRLQE AIAASILRSL ALTVQQPYAL LQQPSLVNLY LQRIVAQQLQ  100
cZ19C1     MATKIFSLLM LLALSACVAN ATIFPQCSQA PIASLLPPYL PSMIASVCEN PALQPYRLQQ AIAASNIPLS PLLFQQSPAL ****SLVQSL VQTIRAQQLQ
cZ19C2                T                                I   I

cZ19A2                G         H                 * * Q             Q               A  L       P       D
cZ19B1                                  GS    S     *  Q         P    Q               P  L               G    T
cZ19AB1    QLVL****** **ANLAAYSQ QQQFLPFNQL AALNSAAYLQ QQQLLPFSQL ***AAAYPR* *QFLPFNQLA ALNSHAYVQQ QQLLPFSQLA AVSPAAFLTQ
cZ19D1     QQLLPTINQV VAANLDAYLQ QQQFLPFNQL AGVNPAAYLQ AQQLLPFNQL VRSPAAFLLQ QQLLPFHLQV VANIAAFLQQ QQLLPFYPQV VGNINAFLQQ  200
cZ19C1     QLVLPLINQV ALANLSPYSQ QQQFLPFNQL STLNPAAYLQ *QQLLPFSQL ***ATAYSQQ QQLLPFNQLA ALNPAAYLQQ QILLPFSQLA AANRASFLTQ
cZ19C2

cZ19A2               A     A  V         N        T
cZ19B1     P       Q V     A            N         V
cZ19AB1    QQLLPFYLHT APNVGTLLQL QQLLPFDQLA LTNPAAFYQQ PIIGGALF
cZ19D1     QQLLPFYPQD VANNVAFLQQ QQLLPFSQLA LTNPTTLLQQ PTIGGAIF
cZ19C1     QQLLPFYQQF AANPATLLQL QQLLPFVQLA LTDPAASYQQ HIIGGALF                                                 248
cZ19C2
```

FIG. 5

```
                                 NH2-
cZ22Alaa  MATKILALLA LLALLVSATN AFIIPQCSLA PSASIPQFLP PVTSMGFEHP AVQAYRLQLA LAASALQQPI AQLQQQSLAH LTLQTIATQQ QQQQFLPSLS
cZ22Blaa        S        FA      S     .     SI            A             Q  I   V                    I       *       A
cZ22C2aa  Start:         F                    I                L         Q      V      N             I       *       A      100

cZ22Alaa  HLAMVNPVTY LQQQLLASNP LALANVAAYQ QQQQLQQFMP VLSQLAMVNP AVYL***QLL SSSPLAVGNA PTYLQQQLLQ QIVPALTQLA VANPAAYLQQ
cZ22Blaa          A                   V N          L  A           A  QQQ            A         E                   V
cZ22C2aa  Q DV    A                                L  A           A  QQQ                                                 200
                                                                                 -COOH
cZ22Alaa  LLPFNQLAVS NSAAYLQQRQ QLLNPLAVAN PLVATFLQQQ QQLLPYNQFS LMNPAL**QQ PIVGGAIF
cZ22Blaa         TM                            A    *         R      V SR
cZ22C2aa         T                    E P      A    *        S          SW                                              268
```

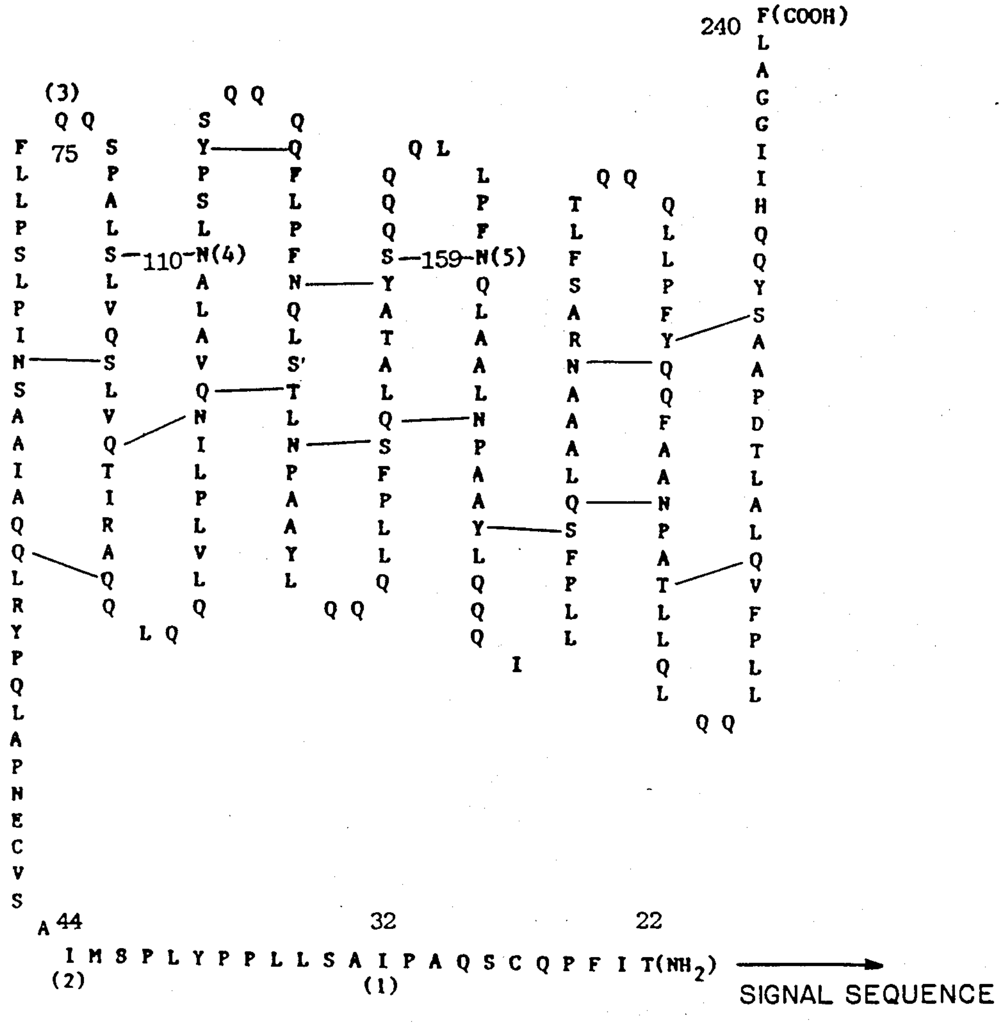

FIG. 7

SITE SPECIFIC MODIFICATION OF Mr 19,000 ZEIN PROTEIN

*[Figure 7: Diagram showing the amino acid sequence of the Mr 19,000 zein protein with site-specific modification positions marked at residues 44, 75, 110, 159, 240 and labeled insertion points (1), (2), (3), (4), (5). Signal sequence shown at the N-terminus: IMSPLYPPLLSAIPAQSCQPFIT(NH₂), with arrow indicating signal sequence direction. The protein sequence is arranged in vertical columns showing the repeating helical domains characteristic of zein, terminating at F(COOH) at position 240.]*

MODIFIED ZEIN GENES CONTAINING LYSINE

This is a continuation of U.S. application Ser. No. 929,751, filed Nov. 12, 1986, now abandoned, which in turn is a continuation-in-part of U.S. application Ser. No. 744,913, filed June 12, 1985, now abandoned.

INTRODUCTION

Seed storage proteins are the major source of protein in a vegetarian diet. Most seed storage proteins are nutritionally incomplete in that they lack one or more of the essential amino acids for proper nutrition of higher animals including man. Reliance on a single source of vegetable protein to meet dietary needs leads to deficiency conditions. For example, the cereal seed storage proteins typically lack the essential amino acid lysine, and overdependence on a cereal, notably corn, for dietary protein is in part responsible for the condition of malnutrition known as kwashiorkor.

When using corn as feed or in the human diet, it is therefore necessary to supplement the diet with another protein source or with lysine itself. Such supplemental feeding is not always convenient or economically feasible. The present invention provides a modified zein which contains lysine. The modified zein serves as a nutritionally balanced source of protein. The modified zein can be provided in any form acceptable to the intended consumer, e.g., as a single cell protein, or as the seed storage protein of a genetically modified plant, which may be maize, soybean, sunflower or other plant species carrying and expressing a gene encoding the modified zein, either in its seeds or other edible tissues.

MAIZE ZEIN PROTEINS

The storage proteins of maize seed consist of a group of prolamine proteins called zeins. (For review, see Larkins, B., *Genetic Engineering of Plants,* T. Kosuge, C. P. Meredith and A. Hollander eds., Plenum Press, New York 1983, pp. 93–118.) The zeins are water-insoluble, but are soluble in alcohol. Zein proteins are synthesized by membrane-bound polyribosomes in the developing endosperm and are deposited as aggregates called protein bodies within the rough endoplasmic reticulum (RER). Because of this, one observes RER membranes surrounding protein bodies in electron micrographs of maize endosperm. It is often difficult to observe continuity between membranes surrounding the protein bodies and the RER, but previous studies have shown the existence of similar populations of polyribosomes on the surface of both membranes (Larkins, B. A. and W. J. Hurkman (1978) Plant Physiol. 62:256–263). Perhaps the most convincing evidence that zein protein bodies form simply by protein aggregation within the RER is the observation that structures with the same physical characteristics as protein bodies can be isolated from *Xenopus laevis* oocytes previously injected with zein mRNAs (Hurkman et al. (1981) J. Cell. Biol. 89:292–299).

A 2-dimensional gel analysis of the alcohol-soluble proteins contained within the protein bodies reveals a mixture of polypeptides. The most abundant of these have apparent molecular weights of 22,000 and 19,000, but there are also other polypeptides of 27,000, 15,000 and 10,000 daltons. There is significantly more charge heterogeneity among the Mr 22,000 and Mr 19,000 zeins than the small molecular weight zein proteins.

Marks and Larkins (1982) J. Biol. Chem. 257:9976–9983, and Pederson, et al. (1982) Cell 29:1015–1026 have constructed cDNA clones of zein mRNAs and determined the DNA sequence for representative Mr 22,000, Mr 19,000, and Mr 15,000 zein proteins. The sequence for an Mr 19,000 zein has also been reported by Geraghty et al. (1981) Nucleic Acids Res. 9:5163–5174. From knowledge of the DNA sequence it has been possible to determine the complete primary amino acid sequence of the polypeptides and compare them for structural similarities.

This analysis revealed that the zeins were significantly larger than expected based on their mobility on SDS polyacrylamide gels. Zein proteins that had been estimated to have molecular weights of 22,000 and 19,000 were found to be closer to 27,000 and 23,000, respectively (Table I). This analysis also confirmed the presence of signal peptides on the zein proteins (FIG. 1). These signal sequences were previously demonstrated to be removed when the protein is transported into the lumen of the RER (Larkins al. (1979) Proc. Natl. Acad. Sci. USA 76:6448–6452).

TABLE I

Amino Acid Composition of Maize Zein Proteins

| Apparent Molecular Weight | [a]Zein α Mr 22,000 | [b]Zein β Mr 19,000 | Zein Mr 15,000 |
|---|---|---|---|
| Amino Acid | | | |
| Leu | 42 | 44 | 15 |
| Gln | 41 | 39 | 28 |
| Ala | 34 | 31 | 18 |
| Pro | 22 | 21 | 13 |
| Ser | 18 | 15 | 11 |
| Phe | 8 | 13 | 0 |
| Asn | 13 | 9 | 2 |
| Ile | 11 | 9 | 1 |
| Tyr | 6 | 8 | 16 |
| Val | 17 | 6 | 4 |
| Gly | 2 | 4 | 12 |
| Thr | 7 | 4 | 5 |
| Arg | 4 | 3 | 7 |
| His | 3 | 3 | 4 |
| Cys | 1 | 2 | 6 |
| Glu | 1 | 1 | 5 |
| Met | 5 | 1 | 11 |
| Asp | 0 | 1 | 4 |
| Lys | 0 | 0 | 0 |
| Trp | 0 | 0 | 1 |
| TOTAL | 225 | 214 | 163 |

[a]Marks and Larkins (1982) J. Biol. Chem. 257:9976–9983
[b]Pedersen et al. (1982) Cell 29:1015–1026

The amino acid composition predicted from the polypeptide sequence is similar to that previously found for mixtures of zein proteins (Lee et al. (1976) Biochem. Genet. 14:641–650). Glutamine, leucine, proline, alanine, and serine account for the majority of the amino acids, and lysine and tryptophan are absent or present in very small amounts (Table I). It is interesting to note that methionine, which is deficient in most legume storage proteins, accounts for a significant percentage of the Mr 15,000 zein. In fact, cysteine and methionine account for 11% of the total amino acids in this polypeptide.

A particularly interesting feature of the protein sequence is the occurrence of a conserved, tandemly repeated peptide in both of the Mr 22,000 and Mr 19,000 zeins (FIG. 1). The first of these repeat sequences begins 35–36 amino acids after the $NH_2$-terminus, and is repeated nine times in each polypeptide. The COOH-terminal sequence following the repeats is slightly longer in the Mr 22,000 zeins; this accounts for the size difference between the two polypeptides. Most of the amino acids in these repeats are nonpolar, while the repeated peptide is sequentially polar, nonpolar, polar, nonpolar, polar.

Circular dichroism measurements of mixtures of zein proteins indicate from 45–55% α-helical structure (Argos et al. (1982) J. Biol. Chem. 257:9984–9990) and this percentage correlates well with the proportion of amino acids in these repeated peptides. To determine if the repeats have the potential to form α-helices their amino acid sequences were compared with those found in proteins having α-helical structure (Argos et al., supra). Although a comparison to soluble proteins shows little propensity for these repetitive sequences to be α-helical, they do have α-helical properties when compared with sequences found in some hydrophobic proteins. In view of the hydrophobic nature of zein proteins, it seems reasonable to predict an α-helical structure for them.

Assuming that these are α-helices, a model showing how the nine repeats could be organized into a 3-dimensional structure has been published. The model predicts that when the consensus repeat is placed in an α-helical wheel the polar amino acids are distributed at three symmetrical sites. Considering that the repeats are tandem, if they fold back upon one another in an antiparallel arrangement, two polar groups in each repeat can hydrogen bond with each of two adjacent repeats. The nine helices would then interact to form a roughly cylindrical, rod-shaped molecule. The cylinder would collapse in the center to accommodate the non-polar tails of the amino acids. As these protein molecules associate within the endoplasmic reticulum, the third polar group, which is on the surface of the helix, would hydrogen bond to a different zein molecule. This arrangement also allows the glutamine residues, which lie at the ends of the helices, to hydrogen bond with neighboring protein molecules in the protein body. FIG. 7 provides a two-dimensional representation of the proposed model.

The published model explains many of the physical properties of the proteins (Argos et al supra), although it has not been confirmed by x-ray diffraction patterns of protein crystals. If the interaction of these α-helices is important in structuring the polypeptide and aggregating it into a protein body, it would appear that altering the amino acid sequence of these repeated regions could deleteriously affect the protein's structure. Larkins (1983) supra, stated that it would seem more advantageous to change the $NH_2$-terminal or COOH-terminal turn sequences which lie outside the repeat structures.

SUMMARY OF THE INVENTION

The invention includes modified 19 kd and 22 kd zeins containing lysine, modified structural genes encoding protein precursors to said modified zeins and various genetic constructs and vectors comprising these modified genes. Modified zeins can comprise single or multiple substitutions of lysine within the internal repeated region of the zein. Modified zein can additionally comprise substitutions of lysine in the $NH_2$-terminus and/or -COOH terminus. It is preferred that substituted lysine replace polar or moderately non-polar amino acids. Modified zeins can be prepared by expression of modified zein genes, in which a lysine codon has been appropriately substituted within the DNA encoding the zein. Zeins modified in these ways resemble normal unmodified zeins in molecular weight, ability to form protein bodies within the rough endoplasmic reticulum of a host cell, and solubility in alcohol.

BRIEF DESCRIPTION OF THE FIGURES

FIG. 1 provides a summary of the consensus amino acid sequence of zein proteins exemplified by the sequences of 19 kd and 22 kd zeins. A particularly interesting feature of these sequences is a conserved, tandemly repeated peptide found in both the 19 kd and 22 kd zeins.

FIG. 2 shows the nucleotide sequence of clones of 19 kd zeins. Included in this figure is the previously reported sequence of gZ19AB1 (Pederson et al., 1982). The complete sequence of gZ19AB1, cZ19D1 and cZ19C2 are given. The sequences of the cZ19A2 and cZ19B1 begin after the "start:" and only nucleotides that are different from those of gZ19AB1 are shown. Similarly, cZ19C1 sequence begins after the "start:" and only those nucleotides that vary from cZ19C2 are shown. The symbol "An" indicates a sequence terminating in a poly (A) tail and putative polyadenylation sites are underlined. Asterisks indicate positions where gaps were introduced in the sequence to maximize homology. Positions corresponding to the initiating methionine (Met) and the $NH_2$- and -COOH termini of the encoded polypeptide are indicated.

FIG. 3 gives the nucleotide sequence of clones for the 22 kd zeins. Nucleotides are numbered starting with the first base of the initiator codon and are indicated on the right-hand margin. The complete nucleotide sequence of cZ22Ais given, but only variable nucleotides at corresponding positions are listed for other clones. Asterisks indicate positions where gaps were introduced in the sequence to maximize homology. The positions of the first nucleotides for cZ22B1 and cZ22C2 follow "start:". The symbol "An" indicates the position at which a sequence terminates in a poly (A) tail. Positions corresponding to the initiating methionine (Met) and the $NH_2$- and -COOH termini of the encoded polypeptide are indicated.

FIG. 4 gives the amino acid sequences of 19 kd zeins deduced from the clones of FIG. 2. The complete amino acid sequences deduced from gZ19AB1, cZ19D1 and cZ19C1 are given using standard nomenclature (see Table 2). Only amino acid residues for cZ19A2 and cZ19B1 that differ from gZ19AB1 are shown as are only amino acid residues for cZ19C2 that differ from the sequence of cZ19C1. Asterisks indicate gaps introduced in the amino acid sequence to demonstrate homologies.

FIG. 5 gives the amino acid sequences of 22 kd zeins deduced from the clones of FIG. 3. The complete amino acid sequence deduced from cZ22A1 is given in standard single letter amino acid code (Table 2), but only variable amino acid residues at corresponding positions are listed for the other sequences. The positions of the $NH_2$-terminus and -COOH terminus of the mature proteins are indicated.

FIG. 7 provides a two-dimensional representation of the proposed structural model of 19 kd and 22 kd zeins, exemplified for the 19 kd zein, Z19C1. Cross-bars show hydrogen bonds between residues on adjacent domains of the α-helix which are postulated to stabilize the highly compact central position having repeated segments of amino acid sequence. Specific amino acid sites at which lysine has been substituted are indicated by the numbers 1–5. Modified zein clones containing single and double lysine substitutions are listed. The nomenclature of modified pre-zein clones is as follows: pMZ=modified zein; IK=isoleucine replaced by lysine; QK=glutamine replaced by lysine; and NK=asparagine replaced by lysine. The numbers refer to the amino acid that was changed, with numbering, as shown, starting at the initiation codon (ATG) of the signal sequence.

DETAILED DESCRIPTION OF THE INVENTION

Figure 6A:
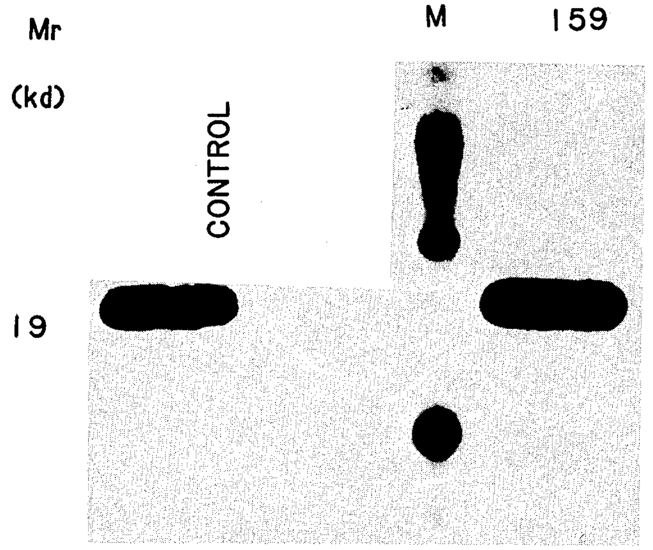
FIG. 6 (*a* and *b*) show the results of SDS acrylamide gel electrophoresis of translation products of modified pre-zein mRNA. Translation was carried out via microinjection of frog oocytes and protein products were monitored by incorporation of tritiated leucine. Membrane fractions were isolated from oocytes and ethanol soluble proteins extracted for analysis. Control lanes represent products of translation of the unmodified zein Z19C1. Lanes representing products of translation of modified zeins are labelled with the number(s) of the amino acid position at which lysine substitution was made. The intensity of the protein bands in this figure is mainly a reflection of gel loading.

Conventional nomenclature for the zeins refers to their nominal molecular weights based on mobility on SDS polyacrylamide gels. Although the actual molecular weights, deduced from the nucleotide sequences of the genes encoding these proteins is somewhat larger, as stated supra, the proteins will be referred to in terms of the conventional nomenclature. Zeins of molecular weight of approximately 15 kd, 19 kd and 22 kd have been reported. The present invention relates to the 19 kd and 22 kd zeins. The principles of amino acid substitution are exemplified herein in connection with a 19 kd zein. Similar modifications can be made in the 22 kd zeins without substantially affecting their zein-like properties.

An important operating principle maintained throughout is that a modification must not interfere with the ability of the modified protein to function as a storage protein in maize endosperm. The unusual solubility properties of zein, the ability to be translocated within the cell and the ability to form characteristic protein bodies are considered important criteria for correct functioning of a modified zein protein. Hurkman et al. (1981) have demonstrated that the foregoing criteria can be measured in the frog oocyte expression system. Thus, authentic pre-zein mRNA can be injected into frog (*Xenoous laevis*) oocytes wherein translation yields a protein which accumulates in rough endoplasmic reticulum in protein bodies resembling those found in maize endosperm tissue. The term "modified zein" is therefore reserved for zein proteins having an amino acid sequence which is not naturally occurring, which behave similarly to authentic zeins in a frog oocyte expression system and which are soluble in alcohol. The term "pre-zein" denotes the primary translation product of mRNA comprising a zein coding sequence, said primary translation product comprising an additional $NH_2$-terminal sequence not found in mature zein isolated from protein bodies. The additional $NH_2$-terminal sequence is believed to function as a signal peptide which aids in intracellular compartmentalization of the translation product. The terms "modified pre-zein" and "modified pre-zein gene" as used herein have the same meanings with respect to the modified sequences as those used in connection with the unmodified sequences, the only difference being related to changes in the primary amino acid sequences described herein.

An important feature of the present invention is based upon the unexpected finding that the substitution of a lysine within the repeated segments of the molecule yields a modified, lysine-containing zein product that meets the functional and physical criteria described, supra. The invention has been exemplified by the modification of a DNA encoding a 19 kd pre-zein gene such that the coding sequence encodes a lysine in the place of an amino acid of the naturally-occurring sequence.

In the examples, the conversion of asparagine residue to lysine at loci within the repeated portion of the sequence yielded lysine containing modified zein which behaved normally when translated in frog oocytes. The results demonstrate that, contrary to expectation, substitution of a lysine for an amino acid in the repeated portion of the molecule is tolerated without detrimental effect to zein function and properties. It will be understood by those of ordinary skill in the art, following the teachings of the present invention, that modifications other than those exemplified can be used to introduce a desired modification in amino acid composition while retaining the functional and physical properties of zein. Amino acid substitutions other than lysine for asparagine, especially those which do not substantially modify the hydrophobicity of the repeated regions may be introduced. An important operating principle is to preserve the overall hydrophobic character of the internal repeats so as to preserve their character as domains responsible for establishing the tightly folded configuration of the zein molecule. Since lysine is protonated at intracellular pH levels, lysine replacement of a highly non-polar amino acid is likely to be more disruptive than replacement of a polar, or moderately non-polar amino acid. In addition, amino acid residues that are attractive candidates for replacement will be located in less conserved regions of the repeated sequences. Such less conserved (divergent) regions can be identified by comparisons of several 19 kd or 22 kd zein sequences. Besides amino acid substitution within the repeated sections, single amino acid insertions can be employed, as well as substitutions in the segments connecting the domains of repeated sequences. Also, insertions and substitutions can be made in both the COOH-terminus and the $NH_2$-terminus of the zein molecule. In particular, the substitution of a lysine for a glutamine within the segment postulated to connect two repeated segments yields a structure having the required properties. Multiple substitutions of lysines within the repeated sequences as well as combinations of lysine substitutions in either the $NH_2$-terminus or the -COOH terminus yield proteins having the required properties. An upper limit to the number of lysines which may be introduced into a modified 19 kd or 22 kd zein has not been determined. A determination of an upper limit is not critical, however, because as little as one lysine residue per modified zein molecule can be sufficient to confer a valuable nutritional benefit. Regulation of the amount of lysine produced by cells or tissues expressing a modified zein coding sequence can be achieved in one of two ways: by increasing the number of lysine residues per molecule or by increasing the number of molecules synthesized per cell. The latter can be achieved according to well known principles in the art, using an appropriate promoter whose activity is sufficient to insure the desired level of gene expression in the desired host cell.

Means for modifying a 19 kd or 22 kd zein structural gene are well known in the art and may be employed according to well known and understood principles in the art to achieve the desired modification. The method of site-specific mutagenesis, using M13-based single stranded DNA vectors and synthetic oligonucleotide primers is exemplified herein, but other means for effecting the desired coding sequence changes may be employed. The technique of site-specific mutagenesis employs the chemically synthesized oligonucleotide corresponding to the coding segment whose modification is desired, with a base substitution at the exact site where a change in the coding sequence is desired. The synthetic oligonucleotide is allowed to hybridize with single stranded DNA comprising its complement, then used to prime DNA synthesis of a new coding strand incorporating the desired base change. When the technique is being used to alter a sequence lying within a region known to contain repeats, care must be taken to insure that the oligonucleotide binds to the template at the desired site. The oligonucleotide must be either sufficiently unique or sufficiently long to prevent mispairing.

The DNA encoding native, or unmodified, zein may be cloned as cDNA or genomic DNA. Although maize contains a number of genes encoding both 19 kd and 22 kd zeins, none has been found to date which contain introns. Consequently, the modification of cDNA is an entirely feasible strategy even if the end result desired is to reincorporate the modified coding sequence into the maize genome to produce genetically modified maize containing nutritionally balanced zein.

A variety of systems for expressing modified zein can be used. A structural gene encoding modified pre-zein may be combined with a promoter known to provide adequate levels of expression in the chosen host cell. The host cells may be any host cell in which expression of modified zein is or can be made compatible, including bacteria, fungi, yeasts, plant cells and animal cells. For example, a modified pre-zein structural gene, as exemplified herein, can be combined with the phaseolin promoter, which is known to provide tissue-specific expression in plants (Sengupta-Gopalan et al. (1985) Proc. Natl. Acad. Sci. USA 82:3320–3324). The composite gene thus constructed can be introduced to plant cells of a desired species using any of a variety of vectors comprising the T-DNA of *Agrobacterium tumefaciens* Ti plasmid (See Caplan, A. et al. (1983) Science 222:815; Barton, K. A. and Chilton, M. D. (1983) Meth. Enzymol. 101:527; and Leemans, J. et al. (1982) in *Molecular Biology of Plant Tumors,* G. Kahl and J. Schell, eds. Academic Press, NY, p. 537). Depending upon the means used for introducing the composite gene into plant cells, and the host plant cell species chosen, the cells receiving the composite gene can be regenerated to form fertile adult plants according to known techniques. Seeds of the regenerated plant will express the modified zein thereby providing a nutritionally balanced diet with respect to amino acid composition for humans or animals using the seeds of the plant as food. Current techniques for gene transfer and regeneration are available for such agronomically significant crops as tomato, soybean, sunflower and a number of vegetable crops. Furthermore, the number of crops in which gene transfer and regeneration techniques are being developed is continually increasing. Expression of a modified zein need not be confined to seed or endosperm tissue. In some instances it will be desirable to enhance the nutritional value of leaves, stems and other edible vegetative tissues of a plant, to enhance the nutritional value of the plant.

In addition to plants, other organisms, especially single celled organisms, may be genetically altered to produce a modified zein, for example as a convenient form of single cell protein. The properties of zein which make it useful for storage of protein in a highly concentrated and stable form in the maize endosperm are expected to be of value for the production of highly nutritious single cell protein.

Modified pre-zein genes may also be expressed in animal cells. In fact, an animal cell system, frog oocytes, was employed as detailed in the examples, for the purpose of rapidly determining whether a given genetic modification yields a modified zein having the appropriate functional and physical characteristics. In the examples, a modified pre-zein coding segment was cloned into the *E. coli* vector SP6. Recombinant SP6, carrying the inserted pre-zein coding segment, was used as template in an in vitro RNA polymerase-catalyzed reaction to produce messenger RNA encoding modified pre-zein. The RNA preparation was then injected into frog oocytes which, when incubated in an appropriate medium under known techniques and conditions, are capable of translating the injected mRNA. The synthesis of zein or modified zein, as the case may be, was measured by the appearance of a protein band on an electrophoresis gel, after extracting alcohol soluble, aqueous insoluble protein from the oocytes. The appearance of a protein band at a position corresponding to 19 kd or 22 kd, as the case may be, indicated the synthesis of zein, or modified zein by the oocytes. In a second type of assay, the appearance of protein bodies in the rough endoplasmic reticulum of oocytes was observed in oocytes expressing native zein or zein modified according to the invention.

In the course of the experiments described in the examples, it was observed that cDNA which had originally been cloned using the technique of homopolymer tailing resulted, after transcription using the SP6 system, in messenger RNA which was poorly translated. Translation was substantially enhanced by pretreating the cDNA with limited exonuclease digestion to remove the homopolymer tails, prior to cloning into SP6.

The following examples further illustrate the invention. Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art (See, for example, R. Wu, ed. (1979) Meth. Enzymol. 68: R. Wu et al., eds. (1983) Meth. Enzymol. 100, 101: L. Grossman and K. Moldave, eds. (1980) Meth. Enzymol. 65; J. H. Miller (1972) *Experiments in Molecular Genetics:* R. Davis et al. (1980) *Advanced Bacterial Genetics:* R. F. Schleif and P. C. Wensink (1982) *Practical Methods in Molecular Biology;* and T. Maniatis et al. (1982) *Molecular Cloning.*). Abbreviations, where employed, are those deemed standard in the field and commonly used in professional journals of wide circulation such as those cited herein.

Textual use of the name of a restriction endonuclease in isolation, e.g., "BclI" refers to use of that enzyme in an enzymatic digestion, except in a diagram where it can refer to the site of a sequence susceptible to action of that enzyme, e.g., a restriction site. In the text, restriction sites are indicated by the additional use of the word "site", e.g., "BclI site". The additional use of the word "fragment", e.g., "BclI fragment", indicates a linear double-stranded DNA molecule having ends generated by action of the named enzyme (e.g., a restriction fragment). A phrase such as "BclI/SmaI fragment" indicates that the restriction fragment was generated by the action of two different enzymes. Note that the ends will have the characteristics of being either sticky (i.e., having a single strand of protrusion capable of base-pairing with a complementary single-stranded oligonucleotide) or blunt (i.e., having no single-stranded protrusion) and that the specificity of a sticky end will be determined by the sequence of nucleotides comprising the single-stranded protrusion which in turn is determined by the specificity of the enzyme which produces it.

Example 1: Cloninq of double-stranded cDNAs

Zein mRNAs were isolated from membrane-bound polyribosomes of the maize inbred W64A as described by Larkins and Hurkman (1978) and used as templates for double-stranded (ds) cDNA synthesis as described by Buell et al. (1978) J. Biol Chem. 253:2471-2482. S1 nuclease-treated ds-cDNAs were fractionated on a 5% polyacrylamide slab gel. Gel slices that contained cDNAs of 700 or more bases were placed in dialysis bags filled with 1 ml of 0.5X TBE (TBE=0.01 M Tris, pH 8.3, 0.01 M boric acid, 0.01 mM EDTA) and were subjected to an electric field of 50 volts for 2 hours. The ds-cDNA was recovered by ethanol precipitation in the presence of 0.3 M Na acetate. Homopolymer tails of oligo (dC) were added to the ds cDNA using terminal transferase as described by Roychoudhury et al. (1976) Nucleic Acids Res. 3:101-116, and the ds cDNA was annealed to the plasmid pUCs that had been homopolymer tailed with oligo (dG). The recombinant plasmids were used to transform the bacterial strain JM83 that was made competent by the method of Morrison (1979) Meth. Enzymol. 6:326. Bacteria containing recombinant plasmids were identified by the filter hybridization procedure of Grunstein and Hogness (1975) Proc. Natl. Acad. Sci. USA 72:3961-3965, using $^{32}$p-labeled cDNA as a probe. By using the pUC 8-JM83 transformation system (Messing and Vieira (1982) Gene 19:269-276), a 10-fold increase was obtained in cloning efficiency over the pBR 322-HB101 system that was previously used.

The sequences of several 19 kd and 22 kd cDNA clones are shown in FIG. 2 and FIG. 3, respectively. The corresponding amino acid sequences are shown in FIGS. 4 and 5.

FIG. 2 gives the nucleotide sequence of clones for the 19 kd zeins. The nucleotide sequence of gZ19AB1 (previously named ZG99) was previously reported (Pederson et al., 1982). The complete sequences of gZ19AB1, cZ19D1, and cZ19C2 are given. The sequences of cZ19A2 and cZ19B1 are the same as the sequence of gZ19AB1 except as indicated. Likewise, the cZ19C1 sequence is the same as that of cZ19C2, except as indicated.

FIG. 3 gives the nucleotide sequence of clones for the 22 kd zeins. The sequences of cZ22A1 and cZ22B1 (previously named pZ22.1 and pZ22.3, respectively) were previously reported (Marks and Larkins, 1982).

FIG. 4 gives the amino acid sequences deduced from the DNA sequence of clones for the Mr 19,000 zeins (FIG. 2) and FIG. 5 gives the amino acid sequences deduced from DNA sequences of clones for the Mr 22,000 zeins (FIG. 3).

Example 2: Removal of homopolymer tails and cloning in M13

In order to generate efficiently translatable mRNA transcripts of a pre-zein gene or modified pre-zein gene it was discovered that the cloned sequences must be further tailored by removing the homopolymer tails generated during the cDNA cloning process. It was found to be sufficient to remove the homopolymer tail at the 5' end of the pre-zein coding sequence.

For this purpose the pUC8 vector containing the 19 pre-zein coding sequence was cut with EcoRI endonuclease. The EcoRI site of pUC8 lies within the same polylinker as the PstI site into which the pre-zein cDNA was originally cloned. Cleavage with EcoRI cuts the vector at the 5' end of the pre-zein gene. The EcoRI linearized plasmid was incubated with Bal31 exonuclease according to standard techniques for varying degrees of limited digestion. The digested linear plasmid was reisolated and cut with HindIII endonuclease. The HindTTT site of the pUC8 polylinker lies on the 3' side of the pre-zein gene. The resulting HindIII cleavage releases the pre-zein DNA coding insert in the form of a population of molecules having varying numbers of nucleotides removed from the 5' end.

The resulting population of 5'-deleted inserts was then cloned into M13mpl1, previously cut with SmaI and I5 HindIII to generate a unidirectional cloning. Upon ligation of the inserts into SmaI/HindIII cut M13mpl1, the sticky ends generated by HindIII cutting at the 3' end of the insert anneal with the HindIII cut end of the M13 vector while the blunt ends of the insert generated by Bal31 digestion can ligate by blunt end ligation to the SmaI cut end of the M13 vector.

Clones of individual inserts in M13mpl1 were then sequenced at the 5' end of the insert to determine the amount of homopolymer tail removed by the Bal31 digestion. Three clones, representing three different degrees of digestion, were analyzed for ability to provide efficient translation, using the SP6 transcription system and frog oocyte translation system described infra in Example 4. The highest yield of zein was produced from transcripts derived from cDNA in which the entire 5' homopolymer tail had been removed as well as an additional two nucleotides of the 5'-untranslated region of the pre-zein cDNA. Intermediate yields of zein were obtained using clones in which the homopolymer tails were partially removed. Therefore, removal of the homopolymer tail at the 5'-end is of substantial importance for efficient translation.

Example 3: Modification of pre-zein codino region by site-specific mutagenesis

M13 bacteriophage and reagents are available as a kit from Amersham Corp., Arlington Heights, Illinois, together with a handbook of instructions for carrying out various manipulations and isolations of single stranded and RF (double stranded) forms of M13 DNA. The handbook of instructions is hereinafter referred to as the "Amersham handbook." *E. coli* GM119 (dcm-6, dam-3, metB-1 thil, lac Y1 or lac 4Z, gal K2, gal T22, mtl-2, ton A2 or ton A31, tsx-1 or tsx-78, supE44, malR/FIKM) is a widely available *E. coli* strain used herein for the purpose of preparing non-methylated M13 DNA. The use of non-methylated DNA favors retention of the mutagenized strand during replication primed by a synthetic oligonucleotide as described infra.

A culture of *E. coli* GM119 was grown from a single colony to an O. D. of 0.6 at 32° C. in LB medium. Fifty μl of the O. D. 0.6 culture was added to 2 ml prewarmed LB medium and 5 μl of M13 phage suspension was added. The culture was grown overnight or for approximately 16 hours at 32° C. After the incubation, intact cells were removed by centrifugation. The supernatant contained phage from which single stranded M13 template DNA was prepared as described in the Amersham handbook.

Gapped heteroduplex DNA comprising unmethylated (+) (viral) strand and a methylated (−) strand was prepared by an annealing procedure. Minus (−) strand DNA was prepared from M13 RF DNA digested with HindIII and EcoRI endonucleases. The reaction mixture was extracted once with a Tris-EDTA buffer saturated with a chloroform/phenol mixture (equal parts by volume). The aqueous phase was then extracted twice with a 5-fold volume of diethyl ether, 0.2 volumes of 5 mM ammonium acetate and 2.5 volumes of ethanol were added to precipitate DNA during a 10–15 minute incubation in a dry ice-ethanol bath. The precipitate was collected by centrifugation, the supernatant was decanted and the tube containing the precipitate was inverted and allowed to air dry. The dried pellet was redissolved in 20 μl of Tris-EDTA buffer. The annealing reaction was initiated by combining 0.5 μg of (+) strand viral DNA (unmethylated) and 0.2 μg linearized RF DNA in 20 μl of 1x SSC. The mixture was overlayed with 50 μl of mineral oil and placed in a boiling water bath for 2 minutes. Immediately thereafter, the tube was transferred to a 65° bath and incubated for 4 hours or more to allow annealing to occur between the (+) and (−) DNA strands. Following annealing, the aqueous layer was transferred to a new tube and traces of mineral oil removed by two successive extractions with 5 volumes of diethyl ether. Residual ether was removed by applying mild vacuum conditions for 2 minutes The DNA was precipitated by adding 50 μl cold ethanol to the reaction mixture and incubating the mixture for 20 minutes in dry ice-ethanol, collecting the precipitated DNA by centrifugation and air drying as before. The above procedure yields from 0.1 μg to 0.3 μg gapped heteroduplex DNA.

The mutagenic oligonucleotides were prepared according to standard techniques of DNA synthesis. Two mutagenic oligonucleotides were prepared, the first having the sequence GGTAGTTACTTTCGAAGT intended to provide an isoleucine to lysine change at amino acid position 44 of cZ19C1, and the second having the sequence GTAAATTTGTTAACCG, intended to encode the substitution of lysine for asparagine at amino acid position 159 in cZ19C1. The mutagenic oligonucleotides are complementary to the coding sequence surrounding the desired site for mutagenesis. In both cases, the lysine codon AAA replaced the native codon at the substitution site. The air dried heteroduplex mixture was dissolved in 1.5 μl of solution "A" [described by Zoller and Smith, *Methods In Enzymology* Vol. 100, p. 468 (1983)] and 2 μl containing approximately 5 pMole of mutagenic oligonucleotide was added, followed by 7.5 μl of DEPC treated water. (DEPC (Diethylpyrocarbonate) added at about 0.01% (v/v) inactivates RNAse and hydrolyzes to yield traces of ethanol and $CO_2$.) The reaction was heated to 65° C. and incubated at that temperature for 15 minutes. The mixture was then annealed by transfer to room temperature for 20 minutes. To 10 μl of the mixture treated as described, the following were added: 1 μl each of 20 mM solutions of dATP, dCTP, dGTP and dTTP, 1.2 l of 10 mM ATP, 2.5 μl of 200 mM dTT (dithiothreitol), 1 μl DNA polymerase Klenow fragment and 1.2 μl of DEPC treated water. The mixture was incubated for 30 minutes at 22° C. (room temperature). Following incubation, 50 units of T4 DNA ligase was added and the mixture again incubated at 22° C. (room temperature) for a period of 4 hours. The foregoing procedure provided closed circular DNA comprising (+) (viral) strands incorporating the mutated sequence derived from the mutagenic oligonucleotides.

The ligated heteroduplex mixture was used to transform *E. coli* JM103 cells, rendered competent for transformation according to the procedure described in the Amersham handbook. *E. coli* JM103 is widely available from a variety of sources. Two hundred μl of competent cells were mixed with 1 μl, 2 μl, 5 μl or 10 μl of heteroduplex mixture, incubated on ice for 40 minutes, then heat shocked by transfer to 42° C. for 2 minutes, then returned to the ice bath. To each tube was then added 10 μl 100 mM IPTG and 50 mM 2% (w/v) X-gal, 100 μl of JM103 cells to provide a bacterial lawn, and 3 ml of 0.7% (w/v) fresh top agar, the latter kept melted at 50° C. The components of each tube were then quickly mixed and poured onto fresh petri plates containing M9 agar. After overnight incubation plaques were formed which appeared white, or colorless, for those phage containing an inserted zein gene.

The efficiency of the procedure yields from 4% to 10% of mutagenized sequences. Clones in which the mutated sequence have been incorporated were identified by the introduction of a new HindIII site in one case, or the loss of a pre-existing HindIII site in the other case, such that a rapid screening could be undertaken without the need for sequence determination of each clone. The restriction pattern of fragments produced by HindIII cleavage was compared after electrophoretic separation with the pattern of fragments produced by unmodified DNA. The resulting modified pre-zein coding sequences were removed from the M13 vector by an EcoRI-HindIII cut and cloned into the transcription vector SP6 (commercially available, e.g., from ProMega Biotech, Madison, Wisconsin) which had previously been digested with EcoRI and HindIII endonucleases. Modified pre-zein clones are named as shown in FIG. 7.

Similar site-specific mutagenesis techniques were used to prepare other modified pre-zein clones, as listed in FIG. 7. Other single substitutions included a lysine for asparagine at amino acid 110 (clone pMZNK110) prepared using the mutagenic oligonucleotide GACCGTTTCGAAAGAG; a lysine for glutamine at position 75 (clone pMZQK75) prepared using the oligonucleotide CAACAAATTTGTTAGC and a lysine for isoleucine at position 32 (clone pMZIK32) prepared using the oligonucleotide CGAGGATTTCGAAGG. Several double substitutions of lysine were also prepared using the same techniques. The sites at which substitutions were made are indicated by numbers 1–5 in FIG. 7.

Example 4: Transcription and translation of modified pre-zein coding segment

The modified pre-zein coding segments, described in Example 3, were released from the M13 vector by digestion with EcoRI and HindIII endonucleases, and cloned into plasmid SP6, cut with EcoRI and HindIII. The transcription plasmid SP6 is commercially available from ProMega Biotec, Madison, Wisconsin. Other reagents and enzymes used for SP6 transcription are also available from ProMega Biotec. The modified prezein gene was transcribed from the SP6 promoter in a reaction containing the following: 40 ml Tris-HCl pH 7.5, 6 mM $MgCl_2$, 2 mM spermadine, 10 mM dithiothreitol, 1 unit/ml RNAsin (trademark ProMega Biotec, Madison, Wisconsin), 100 $\mu$g/ml bovine serum albumin, 0.5 mM ATP, 0.5 mM TTP, 0.5 mM CTP, 0.1 mM GTP, 0.5 mM 7mGpppG and 15 units SP6 RNA polymerase. After 30 minutes incubation at 40° C., 5 additional units of SP6 polymerase and GTP to form a concentration of 0.5 mM were added. The reaction was continued for 1 hour at 40° C. The DNA template was removed by first adding RNAsin to the final concentration of 1 $\mu$g/$\mu$l and then adding RNAse I to 20 $\mu$g/ml final concentration and incubating at 37° C. for 15 minutes. Under these conditions, approximately 0.2 $\mu$g of mRNA was transcribed per $\mu$g of plasmid DNA.

Figure 6B:
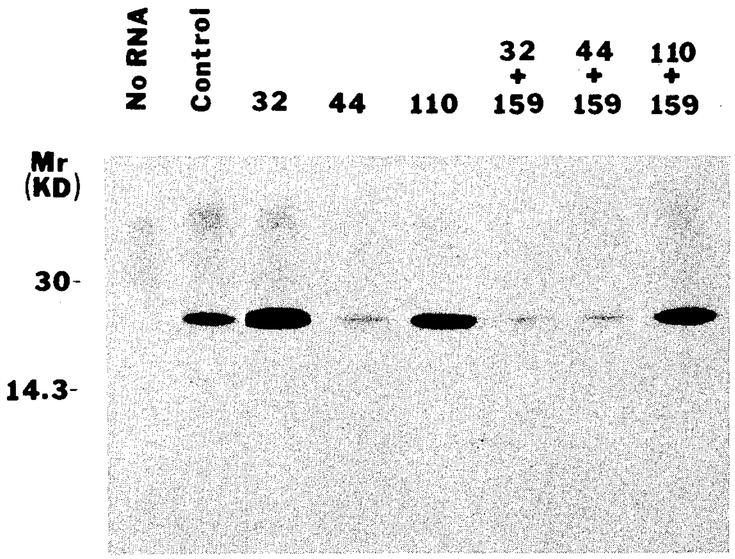

Translation of modified pre-zein mRNA was carried out in frog oocytes microinjected with mRNA as described by Hurkman et al. (1981). Translation was monitored by incorporation of tritiated leucine into protein after microinjection of mRNA. Membrane fractions were isolated from the oocytes and ethanol soluble proteins extracted and analyzed by electrophoresis on SDS acrylamide gels. The results are shown in FIG. 6 (*a* and *b*). The control lanes in both *6a* and *6b* represent the translation product of unmodified Z19C1 zein mRNA, a single protein band corresponding to a molecular weight of about 19 kd as judged by the migration of a series of molecular weight markers (lane M, *6a*). Lanes representing modified zein mRNA translation products in both *6a* and *6b* are labelled using the number of the amino acid at which lysine substitution was made. As shown in FIG. *6a,* with modified pre-zein having a lysine replace asparagine at position 159, a protein of approximately 19 kd was detected. Similarly, with modified pre-zeins with single lysine substitutions at positions 32, 44 or 110 and double lysine substitutions at 32 and 159, 44 and 159 or 110 and 159, a protein having approximately molecular weight of 19 kd was detected. The amount of protein product in FIG. *6a* and *6b,* as indicated by intensity of the band, is not significant. Band intensity is mainly a reflection of gel loading rather than translation efficiency. The results show that unmodified zein was located within the membrane fraction of the oocytes and behaved as an ethanol soluble protein. Further, all single and double lysine substitutions of pre-zein listed in FIG. 7 and shown in FIGS. *6a* and *b* resulted in modified proteins of proper lengths having structures that allowed the modified protein to be translocated to endoplasmic reticulum. The results indicate that zeins modified to include lysine as described herein have translation, translocation and physical properties similar to unmodified zein by all criteria measured in the experiment.

While the invention has been exemplified by a modified 19 kd zein containing lysine, other zeins within the group of 19 kd and 22 kd zeins may be modified, lysine may be introduced by other means, at other locations, by additions and insertions as well as by substitutions within the amino acid sequence, all according to the teachings herein and expedients known to those of ordinary skill in the art mutatis mutandis. Such modifications and variations leading to a modified 19 kd or 22 kd zein comprising a lysine residue are deemed to fall within the scope of the invention, as set forth in the claims.

We claim:

1. A DNA segment encoding a modified 19 kd or 22 kd pre-zein wherein the pre-zein coding sequence comprises a codon for lysine, wherein said codon for lysine is located within the DNA sequence which encodes an internal repeated region of said pre-zein.

2. The DNA segment of claim 1 wherein the pre-zein coding sequence further comprises a second codon for lysine wherein said second codon for lysine is located within the DNA sequence which encodes the -COOH terminus of said pre-zein.

3. The DNA segment of claim 1 wherein the pre-zein coding sequence further comprises a second codon for lysine wherein said second codon for lysine is located within the DNA sequence which encodes the $NH_2$-terminus of said pre-zein.

4. The DNA segment of claim 1 wherein the pre-zein coding sequence further comprises a third codon for lysine wherein said third codon for lysine is located within the DNA sequence which encodes the -COOH terminus of said pre-zein.

5. The DNA segment of claim 1 which is contained in a host cell.

6. The DNA segment according to claim 1, the transcription and translation of which in a host cell yields said zein located within a protein body of the endoplasmic reticulum of said host cell.

7. The DNA segment of claim 1 wherein said codon for lysine is substituted for a codon for a polar or moderately non-polar amino acid.

8. The DNA segment of claim 1 wherein said codon for lysine is substituted for a codon for asparagine.

9. The DNA segment according to claim 1 encoding the 19 kd pre-zein of cZ19C1 modified to contain a lysine codon substituted for an asparagine codon at amino acid codon position 159.

10. A DNA segment according to claim 1 encoding the 19 kd pre-zein of cZ19C1 modified to contain a lysine codon substituted for an asparagine codon at amino acid position 110.

* * * * *